(12) United States Patent
Tran et al.

(10) Patent No.: US 11,090,441 B2
(45) Date of Patent: Aug. 17, 2021

(54) DOSE DIVIDER SYRINGE

(71) Applicant: TELEFLEX MEDICAL INCORPORATED, Morrisville, NC (US)

(72) Inventors: Huy Tran, Riverton, UT (US); Perry Croll, Sandy, UT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 514 days.

(21) Appl. No.: 16/074,415

(22) PCT Filed: Aug. 23, 2016

(86) PCT No.: PCT/US2016/048123
§ 371 (c)(1),
(2) Date: Jul. 31, 2018

(87) PCT Pub. No.: WO2017/035112
PCT Pub. Date: Mar. 2, 2017

(65) Prior Publication Data
US 2019/0030257 A1 Jan. 31, 2019

Related U.S. Application Data

(60) Provisional application No. 62/209,011, filed on Aug. 24, 2015.

(51) Int. Cl.
*A61M 31/00* (2006.01)
*A61M 5/315* (2006.01)
(Continued)

(52) U.S. Cl.
CPC ...... *A61M 5/31595* (2013.01); *A61M 5/2459* (2013.01); *A61M 5/283* (2013.01);
(Continued)

(58) Field of Classification Search
CPC .. A61M 5/283; A61M 5/315; A61M 5/31568; A61M 5/31591; A61M 5/31595
See application file for complete search history.

(56) References Cited

U.S. PATENT DOCUMENTS

| | | |
|---|---|---|
| 3,330,280 A | 7/1967 | Ogle |
| 3,934,586 A | 1/1976 | Easton et al. |

(Continued)

FOREIGN PATENT DOCUMENTS

| | | |
|---|---|---|
| JP | 8-506749 A | 7/1996 |
| JP | 11-151301 A | 6/1999 |
| JP | 2008-539843 A | 11/2008 |

*Primary Examiner* — Rebecca E Eisenberg
(74) *Attorney, Agent, or Firm* — BakerHostetler (57) ABSTRACT

A syringe includes a barrel having an internal surface defining an internal bore therein; a plunger having a distal end disposed within the internal bore of the barrel, and a proximal end disposed outside the internal bore of the barrel; and a dose divider configured to bear on the barrel in response to translation of the plunger relative to the barrel along the longitudinal direction. The dose divider includes a base including a flange that extends at least partly in a radial direction; and at least one column extending away from the base along the longitudinal direction. The at least one column includes a proximal end and a distal end opposite the proximal end, the proximal end of the at least one column being coupled to the base. The at least one column includes a sacrificial portion coupled to a frangible link.

31 Claims, 9 Drawing Sheets

(51) Int. Cl.
    *A61M 5/32*         (2006.01)
    *A61M 5/50*         (2006.01)
    *A61M 5/28*         (2006.01)
    *A61M 11/00*       (2006.01)
    *A61M 5/24*         (2006.01)
    *B67D 3/00*         (2006.01)

(52) U.S. Cl.
    CPC ........ *A61M 5/315* (2013.01); *A61M 5/31591* (2013.01); *A61M 5/32* (2013.01); *A61M 5/50* (2013.01); *A61M 11/007* (2014.02); *B67D 3/0061* (2013.01); *A61M 5/31568* (2013.01); *A61M 2205/582* (2013.01); *A61M 2210/0618* (2013.01)

(56) References Cited

U.S. PATENT DOCUMENTS

| | | | |
|---|---|---|---|
| 4,312,344 A | 1/1982 | Nilson | |
| 5,104,380 A | 4/1992 | Holman et al. | |
| 5,300,041 A | 4/1994 | Haber et al. | |
| 5,833,669 A | 11/1998 | Wyrick | |
| 5,951,526 A * | 9/1999 | Korisch | A61M 5/3129 604/208 |
| 2004/0059294 A1 | 3/2004 | Pelkey et al. | |
| 2005/0137532 A1 | 6/2005 | Rolla | |
| 2006/0195063 A1 | 8/2006 | Lim et al. | |
| 2012/0245530 A1 | 9/2012 | Oden et al. | |
| 2014/0296781 A1 | 10/2014 | Yevmenenko et al. | |
| 2015/0157801 A1 | 6/2015 | Tran et al. | |

\* cited by examiner

DOSE DIVIDER SYRINGE

CROSS-REFERENCE TO RELATED APPLICATIONS

This application is a National Stage of International patent application PCT/US2016/048123, filed on Aug. 23, 2016, which claims priority to U.S. application No. U.S. 62/209,011, filed on Aug. 24, 2015, the disclosures of which are incorporated by reference in their entirety.

TECHNICAL FIELD

The present disclosure relates generally to syringes and, more particularly, to syringes that provide tactile feedback of a quantity of material delivered by operation thereof.

BACKGROUND

Syringes are known for storing and transporting substances with fluid properties such as gases, liquids, pastes, slurries, or any other material that tends to flow in response to applied shear stress. A syringe may include a barrel defining a bore in communication with a port, and a plunger disposed within the barrel. Translation of the plunger away from the port may draw material into the barrel through the port. Alternatively, translation of the plunger toward the bore may expel material from the barrel out of the port.

A syringe barrel may be formed from a transparent or translucent material, such that a position of the plunger within the bore is visible through the barrel. Further, the syringe barrel may include indicia disposed thereon, such that longitudinal alignment of the plunger relative to the indicia may visually indicate a volume of material stored within the syringe.

U.S. Pat. No. 5,104,380 (hereinafter, "the '380 patent") purports to describe a dose metering device for use in conjunction with a syringe and to syringes incorporating such devices. The syringe from the '380 patent includes a body and a dose-setting device mounted on the body and capable of being moved to a selected set position, a latch arranged to retain the setting device in the set position, and means arranged to release the latch to cause the set dose to be expelled. Further according to the '380 patent, movement of the dose-setting device to the selected set position is accompanied by straining of a spring, which, when the latch is released, provides the force for expelling the set dose. However, the latch and spring mechanism of the dose-setting device in the '380 patent may be complex to assemble, expensive to manufacture, require detailed operating instructions for users, or combinations thereof.

U.S. Pat. No. 5,300,041 (hereinafter, "the '041 patent") purports to describe a dose setting and repeating syringe device which allows repetitive injection of a pre-programmed dose amount from a volume of insulin or other pharmaceutical contained within the syringe. A syringe according to the '041 patent includes a mechanical dose programming assembly coupled to a proximal end of a hollow barrel and including a dose ring and a dose plunger slidably mounted onto the dose ring and coupled to a ratchet stem. The dose ring of the '041 patent is threadably mounted onto the proximal end of the hollow barrel and provides adjustable programming of sliding travel of the dose plunger relative to the hollow barrel. However, the mechanical dose programming assembly of the '041 patent may be complex to assemble, expensive to manufacture, require detailed operating instructions for users, or combinations thereof.

Accordingly, there is a need for an improved syringe to address the aforementioned problems and/or other problems in the art.

It will be appreciated that this background description has been created to aid the reader, and is not to be taken as a concession that any of the indicated problems were themselves previously known in the art.

SUMMARY

According to an aspect of the disclosure, a dose divider for a syringe includes a base including a flange that extends at least partly in a radial direction; and at least one column extending away from the base along a longitudinal direction, the longitudinal direction being perpendicular to the radial direction. The at least one column includes a proximal end and a distal end opposite the proximal end, the proximal end of the at least one column being coupled to the base. The at least one column includes a sacrificial portion coupled to a frangible link.

According to another aspect of the disclosure, a syringe includes a barrel having an internal surface defining an internal bore therein; a plunger having a distal end disposed within the internal bore of the barrel, and a proximal end disposed outside the internal bore of the barrel, the proximal end of the plunger being opposite the distal end of the plunger along a longitudinal direction; and a dose divider configured to bear on the barrel in response to translation of the plunger relative to the barrel along the longitudinal direction. The dose divider includes a base including a flange that extends at least partly in a radial direction, the radial direction being perpendicular to the longitudinal direction; and at least one column extending away from the base along the longitudinal direction. The at least one column includes a proximal end and a distal end opposite the proximal end, the proximal end of the at least one column being coupled to the base. The at least one column includes a sacrificial portion coupled to a frangible link.

According to another aspect of the disclosure, a method for delivering a material from a syringe includes breaking away a first sacrificial portion from a column of a dose divider at a first frangible link; installing the dose divider on a proximal end of a plunger, such that a radially inner surface of a remaining column of the dose divider faces the plunger; expelling a first portion of the material from the syringe by bearing a distal surface of a dose divider flange against a proximal surface of the plunger to translate the plunger from a first position to a second position relative to a barrel along a longitudinal axis of the plunger; bearing a distal end of the dose divider against the barrel; and expelling a second portion of the material from the syringe by translating the plunger from the second position to a third position relative to the barrel along the longitudinal axis.

DETAILED DESCRIPTION

Aspects of the disclosure will now be described with reference to the drawing figures, in which like reference numerals refer to like parts throughout, unless specified otherwise.

Figure 1A:
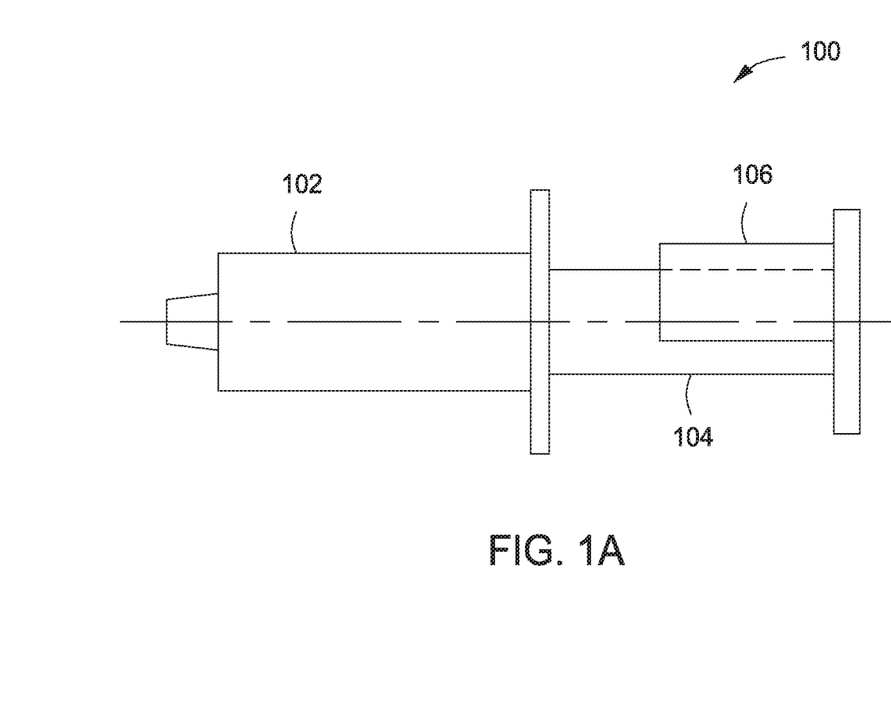
FIG. 1A shows a front view of a syringe, according to an aspect of the disclosure.
Figure 1B:
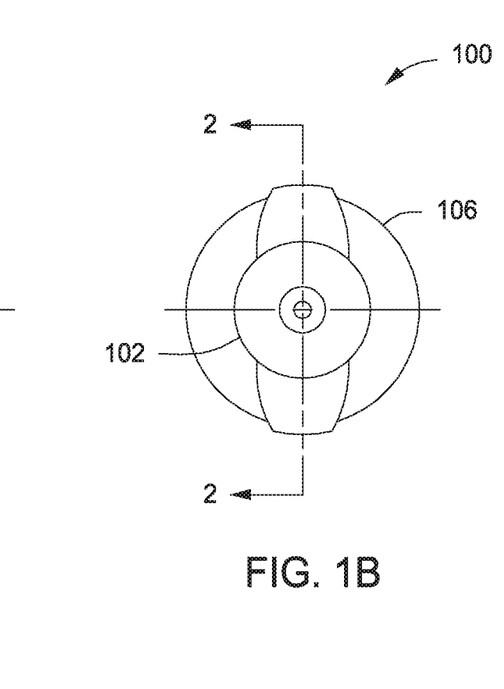
FIG. 1B shows a side view of a syringe, according to an aspect of the disclosure.

Referring to FIGS. 1A and 1B (collectively "FIG. 1"), it will be appreciated that FIG. 1A shows a front view of a syringe 100, according to an aspect of the disclosure; and FIG. 1B shows a side view of a syringe 100, according to an aspect of the disclosure. The syringe 100 includes a barrel 102, a plunger 104, and a dose divider 106. The plunger 104 is disposed at least partly within the barrel 102, and the plunger 104 is configured for sliding engagement within the barrel 102. The dose divider 106 is removably attached to the plunger 104.

Figure 2:
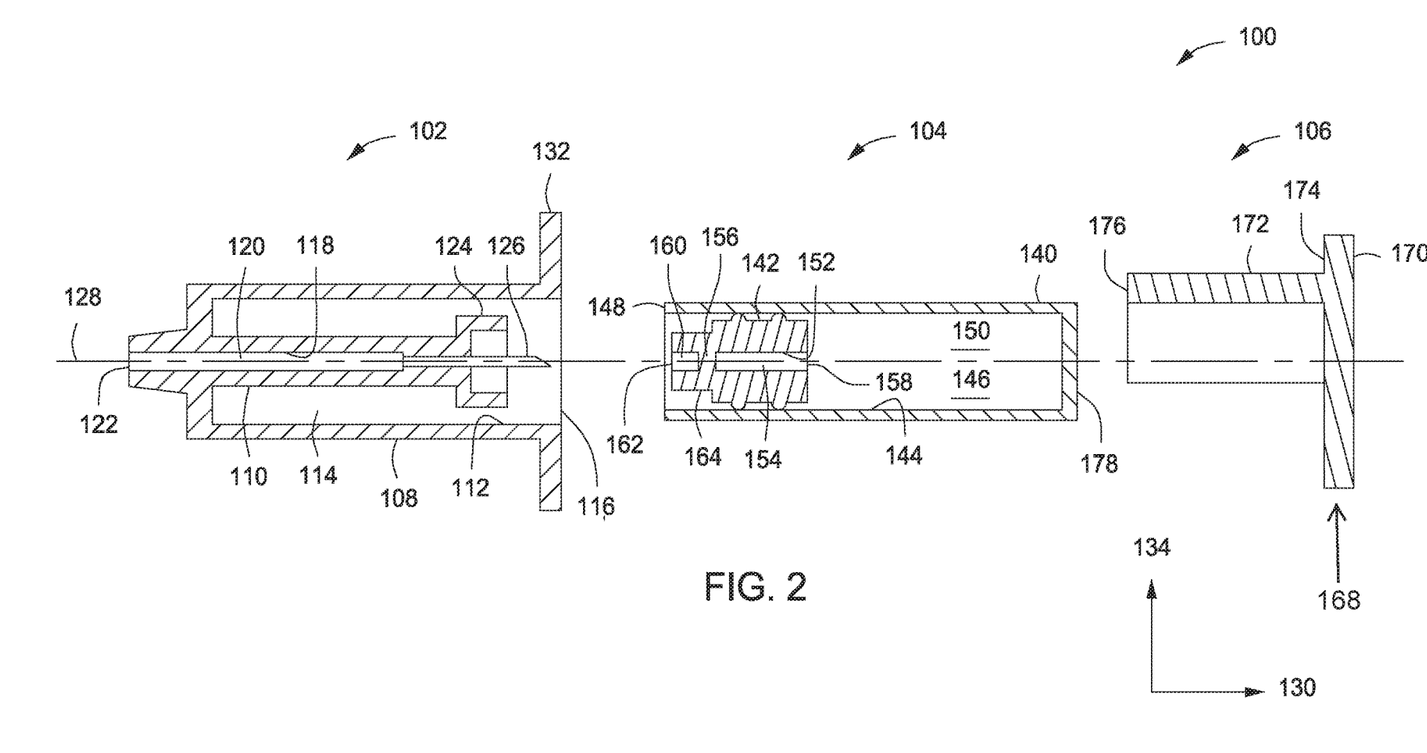
FIG. 2 is an exploded front cross sectional view of the syringe along the section line 2-2, according to an aspect of the disclosure.

FIG. 2 is an exploded front cross sectional view of the syringe 100 along the section line 2-2, according to an aspect of the disclosure. The barrel 102 includes an outer wall 108 and may include an inner stem 110 disposed within the outer wall 108. The outer wall 108 includes an internal surface 112 that defines a barrel cavity 114 therein, and defines a proximal aperture 116 of the outer wall 108. The inner stem 110 includes an internal surface 118 that defines a stem cavity 120 therein, and that defines a distal aperture 122 of the inner stem 110. The distal aperture 122 may be fluidly coupled to an outlet cannula or needle, a fluid atomizer, or any other syringe outlet structure known in the art.

The inner stem may include a stem connector 124 and a cannula 126. The cannula 126 projects through the stem connector 124, and is in fluid communication with the distal aperture 122 via the stem cavity 120. The stem connector 124 may be a threaded connector, a tapered connector, an interference connector, a Luer-type connector, or any other connector known in the art.

According to an aspect of the disclosure, the cannula 126 and the distal aperture 122 are each aligned on a longitudinal axis 128 of the syringe 100, such that the cannula 126 projects away from the distal aperture 122 along a longitudinal direction 130. According to another aspect of the disclosure, the cannula 126 and the stem connector 124 are each aligned on the longitudinal axis 128. However, it will be appreciated that the cannula 126 need not be coaxial with either the distal aperture 122 or the stem connector 124.

The barrel 102 further includes a flange 132 that projects away from the outer wall 108 at least partly in a radial direction 134, where the radial direction 134 is perpendicular to the longitudinal direction 130. According to an aspect of the disclosure, the flange 132 projects away from the outer wall 108 in the radial direction 134.

The plunger 104 may include a vial 140 and a piston 142. The vial 140 includes an internal surface 144 that defines a vial cavity 146, and that defines a distal aperture 148 of the plunger 104. The piston 142 is disposed within the vial cavity 146 in sliding and sealing engagement with the internal surface 144 of the vial 140. Accordingly, the internal surface 144 and the piston 142 may define, at least in part, an internal volume or fluid chamber 150 having a variable volume depending upon a location of the piston 142 within the vial 140 along the longitudinal direction 130.

The piston 142 may include an internal surface 152 that defines a proximal conduit 154 extending from a septum 156 to a proximal aperture 158 of the piston 142, where the proximal aperture 158 is in fluid communication with the fluid chamber 150. The internal surface 152 of the piston 142 may also define a distal conduit 160 extending from the septum 156 to a distal aperture 162. The septum 156 may be configured to block fluid communication between the distal aperture 162 and the proximal aperture 158 via the piston 142.

The piston 142 may also include a piston connector 164 disposed on a distal end of the piston 142. The piston connector 164 may be a threaded connector, a tapered connector, an interference connector, a Luer-type connector, or any other connector known in the art. According to an aspect of the disclosure, the piston connector 164 is complementary to the stem connector 124, such that coupling between the piston connector 164 and the stem connector 124 may fix a spatial relationship between the piston 142 and the inner stem 110 of the barrel 102 along the longitudinal direction 130, the radial direction 134, or combinations thereof. According to another aspect of the disclosure, each of the piston connector 164 and the stem connector 124 are aligned with the longitudinal axis 128. According to another aspect of the disclosure, each of the septum 156 and the cannula 126 are aligned with the longitudinal axis 128.

The dose divider 106 includes a base 168 having a flange 170 and at least one column 172 coupled to the base 168. The flange 170 of the dose divider 106 extends at least partly in the radial direction 134 beyond a radial extent of the at least one column 172. The at least one column 172 extends at least partly in the longitudinal direction 130 from a distal surface 174 of the base 168 to a distal surface 176 of the at least one column 172. The dose divider 106 may be configured to be removably coupled to a proximal end 178 of the vial 140, such that coupling between the dose divider 106 and the vial 140 may fix a spatial relationship between the dose divider 106 and the vial 140 in the radial direction 134, the longitudinal direction 130, or combinations thereof.

According to an aspect of the disclosure, the dose divider 106 is free from any threaded connections with the plunger 104, and free from any ratcheting mechanisms in cooperation with the plunger 104. According to another aspect of the disclosure, the syringe 100 does not include any spring or resilient member disposed between the dose divider 106 and the plunger 104, such that the spring or resilient member acts to bias a position of the dose divider 106 relative to the plunger 104.

Figure 3A:
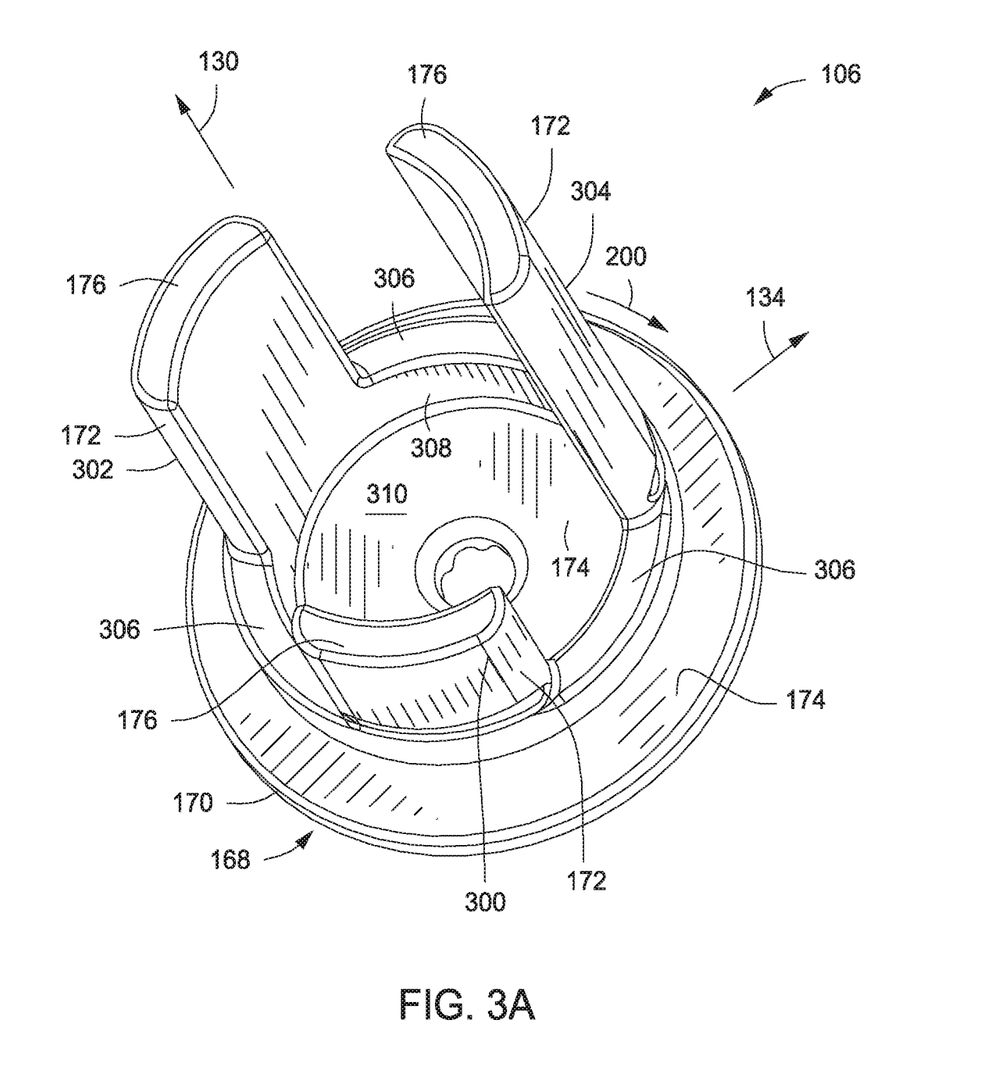
FIG. 3A shows a perspective view of a dose divider, according to an aspect of the disclosure.
Figure 3B:
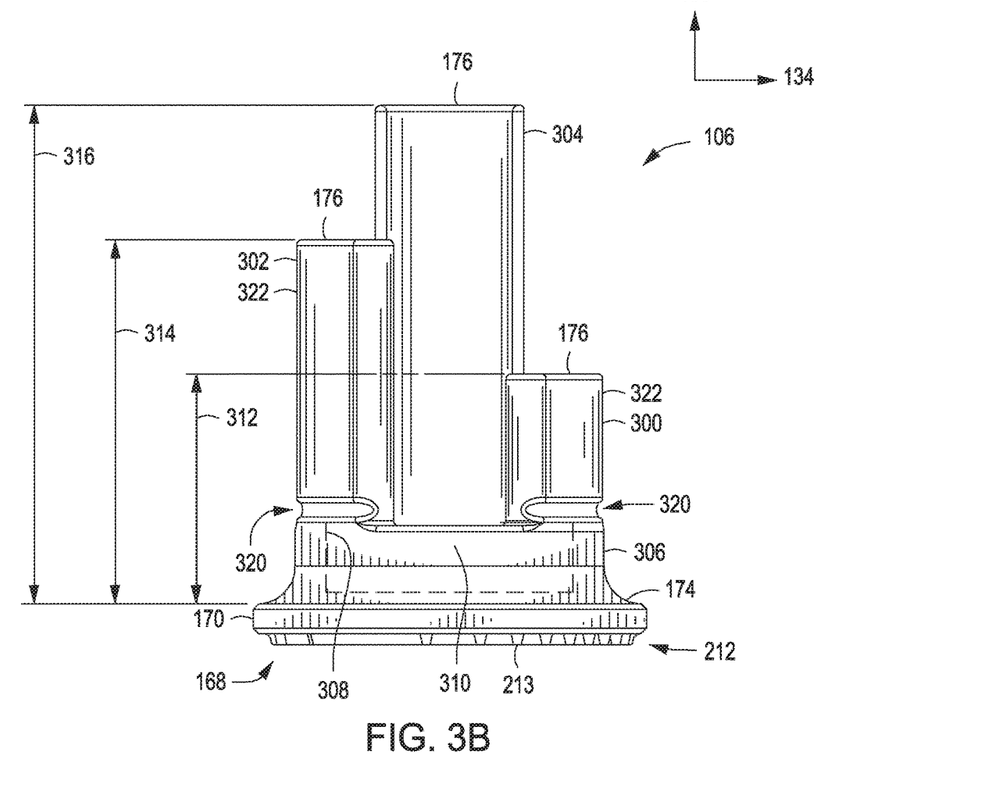
FIG. 3B shows a front view of a dose divider, according to an aspect of the disclosure.
Figure 3C:
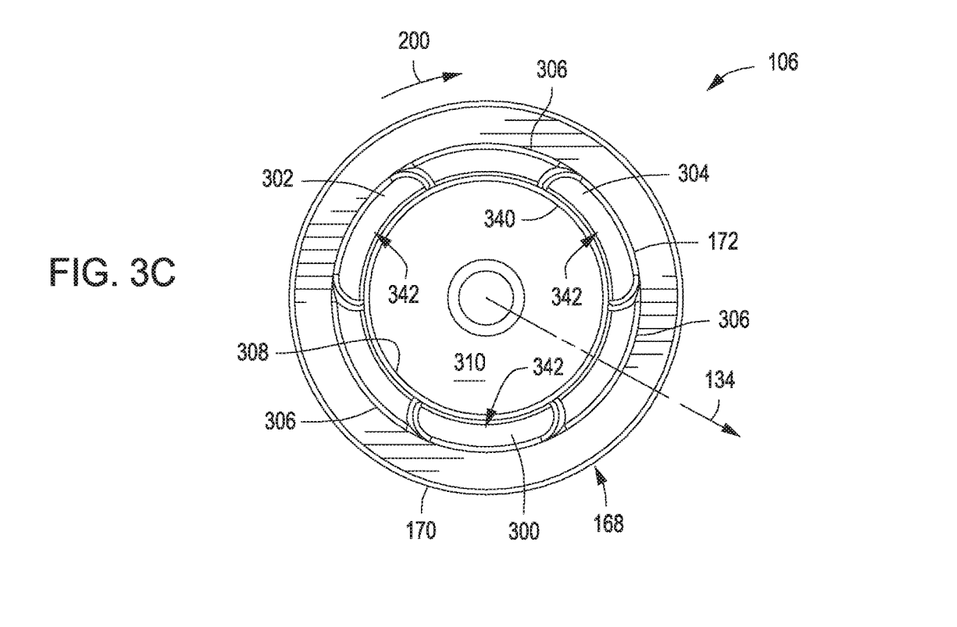
FIG. 3C shows a side view of a dose divider, according to an aspect of the disclosure.
Figure 3D:
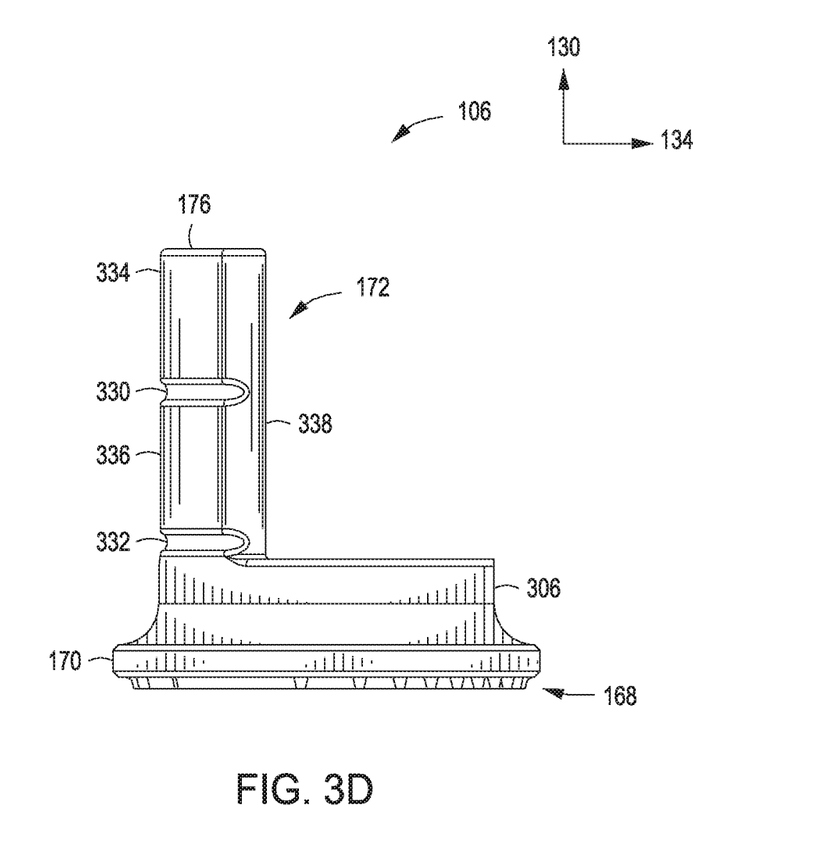
FIG. 3D shows a front view of a dose divider, according to an aspect of the disclosure.

Referring to FIGS. 3A, 3B, 3C, and 3D (collectively "FIG. 3"), it will be appreciated that FIG. 3A shows a perspective view of a dose divider 106, according to an aspect of the disclosure; FIG. 3B shows a front view of a dose divider 106, according to an aspect of the disclosure;

FIG. 3C shows a side view of a dose divider 106, according to an aspect of the disclosure; and FIG. 3D shows a front view of a dose divider 106, according to an aspect of the disclosure.

The dose divider 106 illustrated in FIG. 3, includes a base 168 having a flange 170 and one or more columns 172 coupled to the base 168 and extending away from the base 168 at least partly along the longitudinal direction 130. According to an aspect of the disclosure, the one or more columns 172 extend away from the base 168 along the longitudinal direction 130.

The one or more columns 172 may include a plurality of columns. For example, as illustrated in FIG. 3A, the one or more columns 172 includes a first column 300, a second column 302, and a third column 304 arranged about the base 168 about the circumferential direction 200. However, it will be appreciated that the dose divider 106 may include any number of columns 172 to suit a particular application. According to an aspect of the disclosure, the first column 300, the second column 302, and the third column 304 are equally spaced about the circumferential direction 200 of the dose divider 106.

The base 168 may include a wall 306 that extends away from the base 168 at least partly along the longitudinal direction 130. Further, the one or more columns 172 may be coupled to the base 168 via the wall 306. The wall 306 may be an annular wall that extends around the dose divider 106 about the circumferential direction 200, and an internal surface 308 of the wall 306 may define a recess 310 therein. A depth of the recess 310, along the longitudinal direction 130, may be defined at least in part by the distal surface 174 of the base 168.

The recess 310 may be configured to receive a plunger 104 of a syringe 100. Further, the fit between the plunger 104 and the recess 310 of the dose divider 106 may effect different states of interference therebetween. According to an aspect of the disclosure, the dose divider 106 is free to slide along the plunger 104 in the longitudinal direction 130 but is fixed with respect to the plunger 104 in the circumferential direction 200. According to another aspect of the disclosure, the dose divider is free to slide along the plunger 104 in both the longitudinal direction 130 and the circumferential direction 200.

Referring now to FIG. 3B, a length 312 of the first column 300 along the longitudinal direction 130 may be less than a length 314 of the second column 302 along the longitudinal direction 130. Further, the length 314 of the second column 302 may be less than a length 316 of the third column along the longitudinal direction 130. In FIG. 3B the lengths 312, 314, 316 are defined from the distal surface 174 of the flange 170 to distal ends 176 of the first column 300, the second column 302, and the third column 304, respectively. However, it will be appreciated that the lengths of the columns 172 may be defined relative to other features of the dose divider 106.

One or more of the columns 172 may define one or more frangible links 320 configured to enable breaking a sacrificial portion 322 of the respective column 172 away from the dose divider 106 at a predictable location and in response to a predictable amount of stress exerted onto the frangible link 320. According to an aspect of the disclosure the sacrificial portion 322 of the corresponding column 172 extends from the frangible link 320 away from the base 168.

The frangible link 320 may be characterized by a cross sectional area that is less than an adjacent cross sectional area of the corresponding sacrificial portion 322, a thickness along the radial direction 134 that is less than a radial thickness of the corresponding sacrificial portion 322, a circumferential extent that is less than a circumferential extent of the corresponding sacrificial portion 322, a harder and/or more brittle material than that of a corresponding sacrificial portion 322, combinations thereof, or any other structure known in the art to provide frangible coupling. According to an aspect of the disclosure, the frangible link 320 is configured to sever a sacrificial portion 322 of a column 172 away from the base 168 when a bending moment is applied to the frangible link 320.

According to an aspect of the disclosure, the dose divider 106 includes a plurality of columns 172, and each column of the plurality of columns 172 includes exactly one frangible link 320. However, it will be appreciated that any or all of the columns 172 may include at least one frangible link 320.

The dose divider 106 may include one or more columns 172 having a plurality of frangible links. For example, as illustrated in FIG. 3D, the column 172 may include a first frangible link 330 and a second frangible link 332. A first sacrificial portion 334 may extend from the first frangible link 330 to the distal end 176 of the column 172, and a second sacrificial portion 336 may extend from the second frangible link 332 to the first frangible link 330. Further, a first remaining portion 338 may extend from the first frangible link 330 to the base 168 of the dose divider 160.

Accordingly, breaking the first frangible link 330 removes the first sacrificial portion 334 from the column 172, and leaves the remaining portion 338 of the column 172; and breaking the second frangible link 332 removes the first sacrificial portion 224, the second sacrificial portion 336, or both, from the dose divider 106. According to an aspect of the disclosure, breaking the second frangible link removes substantially all of the column 172 from the dose divider 106. As used herein, removing substantially all of the column 172 from the dose divider 106 may result in small portions or fragments of the second frangible link 332 remaining on dose divider 106, after breaking away substantially the entirety of the corresponding column 172.

According to an aspect of the disclosure, the dose divider 106 includes only one column 172, which has a plurality of frangible links. However, it will be appreciated that the dose divider 106 may include a plurality of columns 172 and that any or all of the plurality of columns may include a plurality of frangible links. Further, although FIG. 3D shows only two frangible links 330, 332, it will be appreciated that a column 172 on the dose divider 106 may include any number frangible links to suit a particular application.

A proximal end 212 of the base 168 may include texturing features 213 to resist sliding of an operator's finger across the proximal end 212 of the base 168 along the radial direction 134, the circumferential direction 200, or combinations thereof. The texturing features 213 may include ridges, bumps, knurling, combinations thereof, or any other surface texturing features known in the art.

Referring now to FIG. 3C, an internal surface 340 of the one or more columns 172 may define a concavity 342 that faces radially inward along the radial direction 134. Further, each column of the one-or more columns 172 may define a concavity 342 that faces radially inward along the radial direction 134. According to an aspect of the disclosure, concavities 342 defined by the columns 172 are configured to couple with the plunger 104 of the syringe 100 in sliding engagement.

Figure 4A:
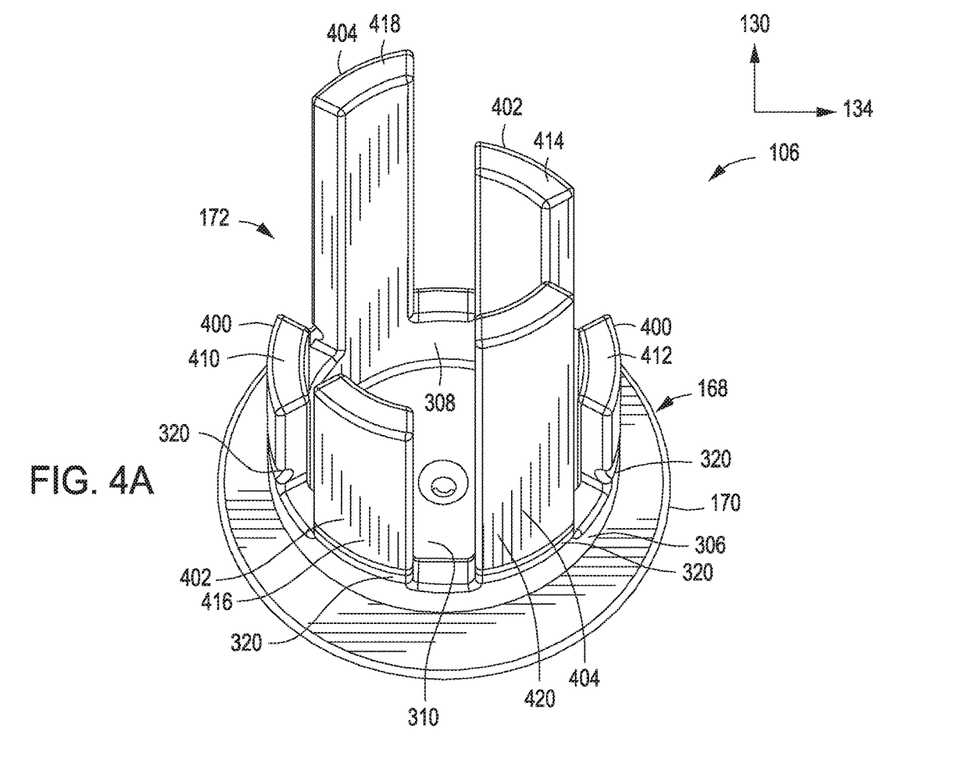
FIG. 4A shows a perspective view of a dose divider, according to an aspect of the disclosure.
Figure 4B:
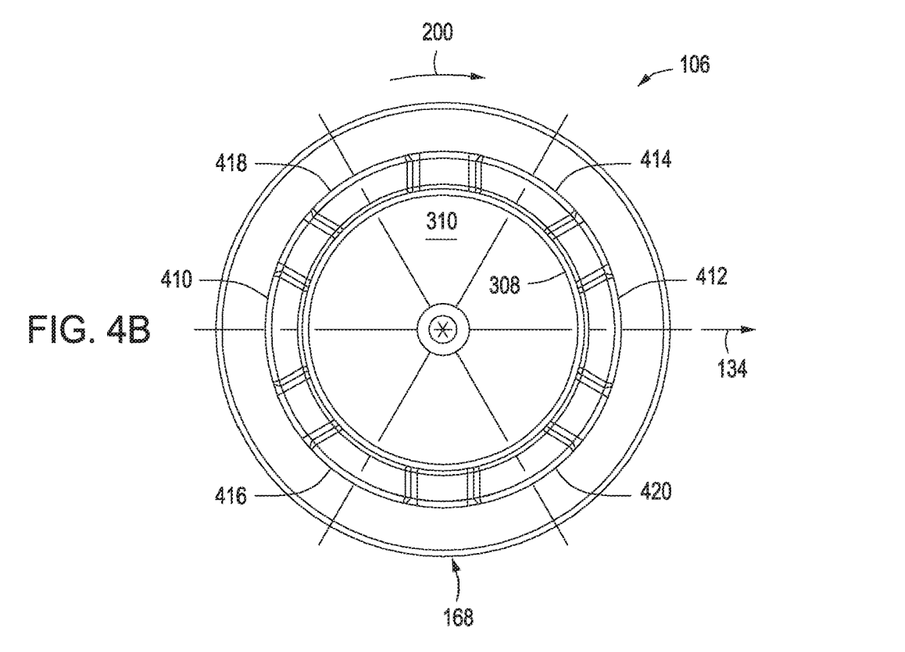
FIG. 4B shows a side view of a dose divider, according to an aspect of the disclosure.

Referring to FIGS. 4A and 4B (collectively "FIG. 4"), it will be appreciated that FIG. 4A shows a perspective view of a dose divider 106, according to an aspect of the disclosure; and FIG. 4B shows a side view of a dose divider 106, according to an aspect of the disclosure. Similar to FIG. 3, the dose divider 106 illustrated in FIG. 4 includes one or more columns 172 coupled to a base 168, where any or all of the one or more columns 172 may define a frangible link 320. However, the one or more columns 172 illustrated in FIG. 4 includes at least one pair of columns. The at least one pair of columns may include a first pair of columns 400, a second pair of columns 402, a third pair of columns 404, or combinations thereof.

The first pair of columns 400 includes a first column 410 and a second column 412, the second pair of columns 402 includes a third column 414 and a fourth column 416, and the third pair of columns 404 includes a fifth column 418 and a sixth column 420. A length of the first column 410 along the longitudinal direction 130 may be substantially equal to a length of the second column 412 along the longitudinal direction 130. A length of the third column 414 along the longitudinal direction 130 may be substantially equal to a length of the fourth column 416 along the longitudinal direction 130. A length of the fifth column 418 along the longitudinal direction 130 may be substantially equal to a length of the sixth column 420 along the longitudinal direction 130. Unless specified otherwise, lengths of columns may be substantially equal when distal ends 176 of each of the columns may simultaneously bear on the barrel 102 during operation of the syringe 100.

A length of the first pair of columns 402 along the longitudinal direction 130 may be less than a length of the second pair of columns 404 along the longitudinal direction 130, and the length of the second pair of columns 404 along the longitudinal direction 130 may be less than a length of the third pair of columns 406 along the longitudinal direction.

The first column 410 may be diametrically opposed to the second column 412 across the base, the third column 414 may be diametrically opposed to the fourth column 416 across the base, the fifth column 418 may be diametrically opposed to the sixth column 420 across the base, or combinations thereof. According to an aspect of the disclosure, the third column 414 is arranged between the first column 410 and the second column 412 about the circumferential direction 200. Additionally, the fifth column 418 may be arranged between the first column 410 and the third column 414.

Operation of the syringe 100 will now be described with reference to FIGS. 5-8.

Figure 5:
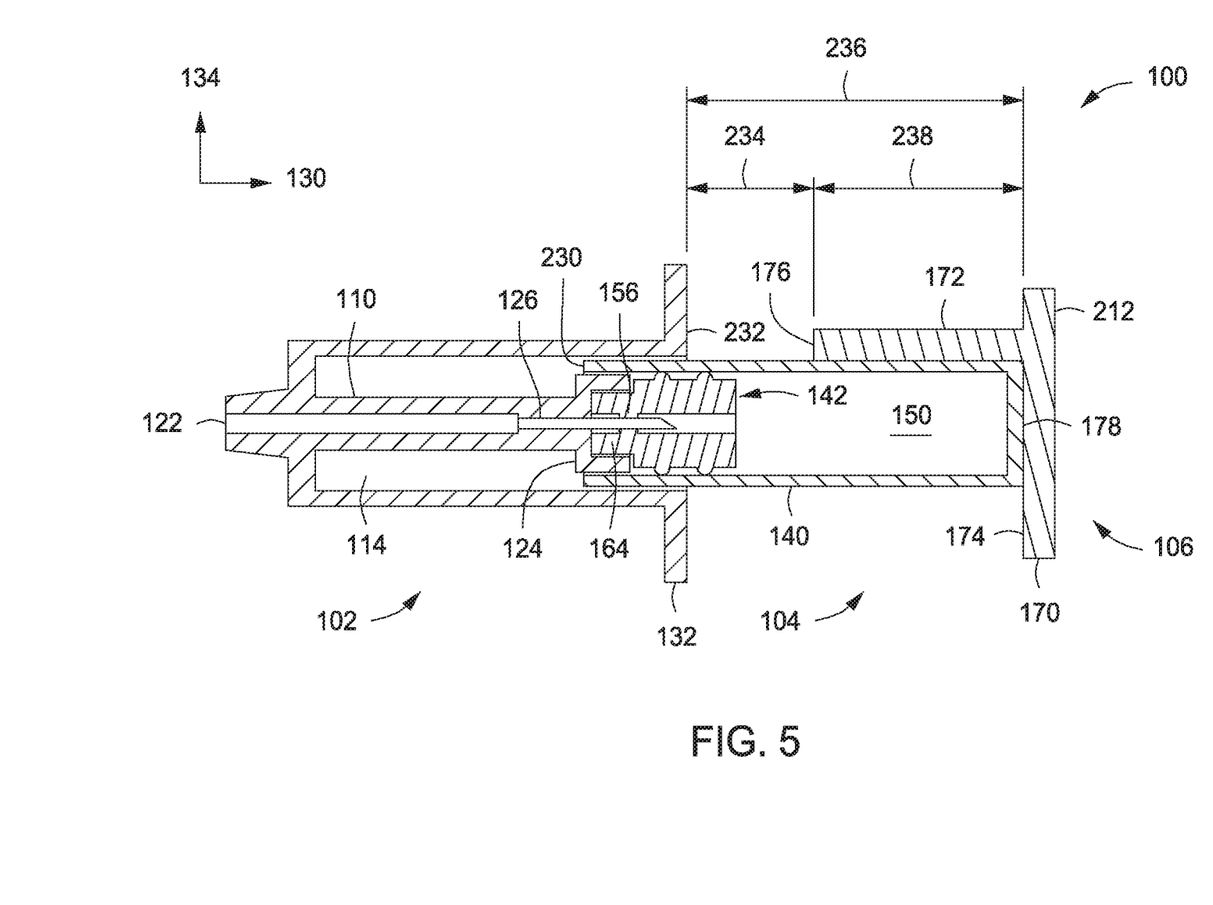
FIG. 5 shows a front cross sectional view of a syringe arranged in a first configuration, according to an aspect of the disclosure.

FIG. 5 shows a front cross sectional view of a syringe 100 arranged in a first configuration, according to an aspect of the disclosure. In FIG. 5, the piston connector 164 is coupled with the stem connector 124, such that the cannula 126 pierces through the septum 156 of the piston 142. In turn, the fluid chamber 150 is in fluid communication with the distal aperture 122 of the stem connector 124 via the cannula 126. A distal end 230 of the vial 140 may be disposed within the barrel cavity 114 when the piston connector 164 is coupled with the stem connector 124.

Referring still to FIG. 5, the dose divider 106 is removably attached to the plunger 104 such that the distal surface 174 of the base 168 of the dose divider 106 bears on the proximal end 178 of the vial 140. It will be appreciated that the distal surface 174 of the base 168 may bear on the proximal end 178 of the vial 140 via intermediate structures disposed therebetween, such that the distal surface 174 of the base 168 does not directly contact the proximal end 178 of the vial 140. According to an aspect of the disclosure, the distal surface 174 of the base 168 bears on the proximal end 178 of the vial 140 in direct contact.

The at least one column 172 of the dose divider 106 faces at least a portion of the vial 140 along the radial direction 134, the circumferential direction 200, or combinations thereof. In the first configuration, the distal surface 176 of the dose divider 106 is separated from a proximal surface 232 of the flange 132 by a distance 234 along the longitudinal direction 130. According to an aspect of the disclosure, a distance 236 from the proximal end 178 of the vial 140 to the proximal surface 232 of the flange 132, along the longitudinal direction, is equal to the sum of the distance 234 and a distance 238 from the distal surface 174 of the base 168 to the distal surface 176 of the at least one column 172.

Before installing the dose divider 106 onto the plunger 104, a user may adjust the remaining length 238 of the at least one column 172 by breaking off a sacrificial portion 334 of the at least one column 172 at a frangible link 330. Further, it will be appreciated that the at least one column 172 may include a plurality of columns, and that a user may adjust the remaining length 238 of any or all of the plurality of columns by breaking off sacrificial portions 334, 336 of individual columns at corresponding frangible links 330, 332.

According to an aspect of the disclosure, breaking off a sacrificial portion 334, 336 of the at least one column 172 includes breaking off an entirety of the at least one column 172, such that the remaining length 238 of the at least one column 172 is substantially zero. Unless specified otherwise, a substantially zero remaining length 238 may include a small portion or fragment of the corresponding frangible link 332 disposed on the distal surface 174 of the base 168 after breaking off the sacrificial portion 336 (see FIG. 3D).

According to another aspect of the disclosure, the distal surface 176 of the dose divider 106 faces the flange 132 of the barrel 102, such that translation of the dose divider 106 toward the flange 132 may result in the distal surface 176 of the dose divider 106 bearing on the flange 132. It will be appreciated that the distal surface 176 of the dose divider 106 may bear on the barrel 102 through intervening components that may transmit a force from the dose divider 106 onto the barrel 102 along the longitudinal direction 130. According to another aspect of the disclosure, the syringe 100 is free from any intervening components between the distal surface 176 of the dose divider 106 and the flange 132 along an projection of the distal surface 176 of the dose divider 106 along the longitudinal direction 130, such that translation of the dose divider 106 toward the barrel 102 may result in the distal surface 176 of the dose divider bearing on the flange 132 in direct contact therebetween.

Translation of the piston 142 toward the proximal end 178 of the vial 140 along the longitudinal direction 130 acts to decrease the volume within the fluid chamber 150, and therefore acts to expel material out of the fluid chamber 150 via the cannula 126 and the distal aperture 122 of the inner stem 110. The piston 142 may be translated toward the proximal end 178 of the vial 140 by translating the vial 140 toward the distal aperture 122 of the inner stem 110 by applying a force on the proximal end 212 of the dose divider 106 along the longitudinal direction 130 toward the distal aperture 122 of the inner stem 110.

According to an aspect of the disclosure, the fluid chamber 150 of the vial 140 is prefilled with a fluid material before the piston connector 164 is coupled with the stem connector 124. According to another aspect of the disclosure, the prefilled material is a medication. However, it will be appreciated that the fluid chamber 150 of the vial 140 may be prefilled with any fluid to suit a particular application of the syringe 100.

Figure 6:
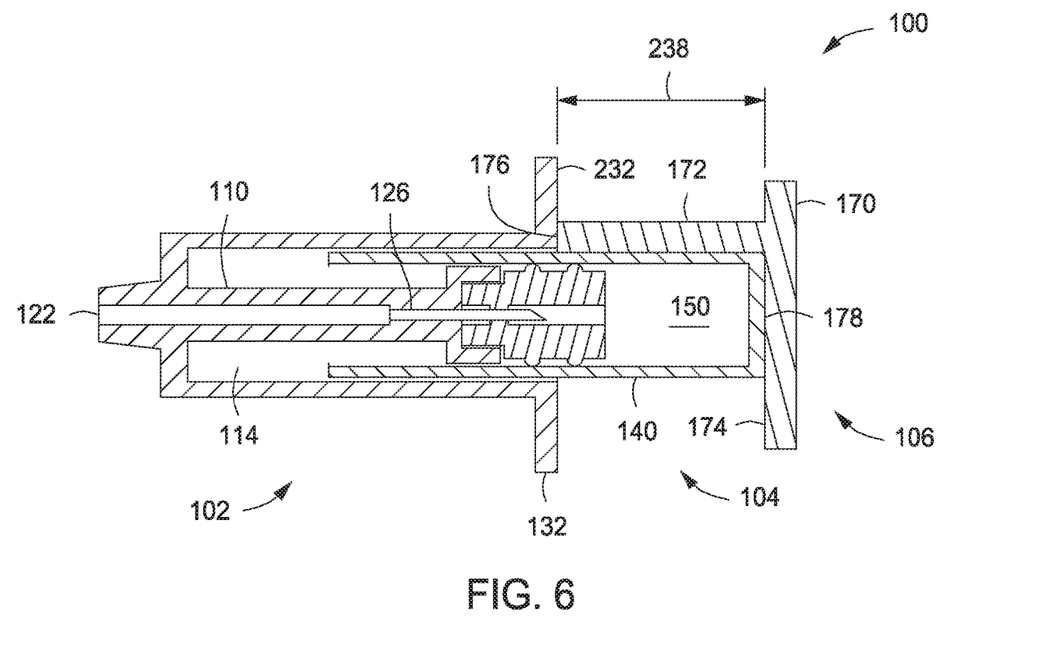
FIG. 6 shows a front cross sectional view of a syringe arranged in a second configuration, according to an aspect of the disclosure.

FIG. 6 shows a front cross sectional view of a syringe 100 arranged in a second configuration, according to an aspect of the disclosure. Similar to the first configuration of the syringe 100 in FIG. 5, the second configuration of the syringe 100 in FIG. 6 has the piston connector 164 coupled with the stem connector 124, such that the cannula 126 pierces through the septum 156 of the piston 142, and the distal surface 174 of the base 168 of the dose divider 106 bears on the proximal end 178 of the vial 140. However, in the second configuration illustrated in FIG. 6, the vial 140 has been translated toward the distal aperture 122 of the inner stem 110, by the distance 234 (see FIG. 5) for example, such that the distal surface 176 of the at least one column 172 of the dose divider 106 bears on the barrel 102. Thus, between the first configuration (see FIG. 5) and the second configuration of the syringe 100, a first portion of the material contained within the fluid chamber 150 is delivered out of the syringe 100 via the distal aperture 122 of the inner stem 110.

According to an aspect of the disclosure, the distal surface 176 of the at least one column 172 bears on the proximal surface 232 of the flange 132 of the barrel 102 when the syringe 100 is arranged in its second configuration. According to another aspect of the disclosure, the proximal end 178 of the vial 140 may be spaced apart from the proximal surface 232 of the flange 132 by the distance 238, when the syringe 100 is in its second configuration.

According to an aspect of the disclosure, a dose divider 106 disposed on the plunger 104 in the second configuration may be removed from the plunger 104 and then a remaining length 238 (see FIG. 5) of at least one column 172 may be shortened by breaking away a sacrificial portion 334 of the at least one column 172 at a corresponding frangible link 330 (see FIG. 3D). Then, the dose divider 106 with the shortened remaining length 238 may be reinstalled on the plunger 104 in the first configuration as shown in FIG. 5, including a distance 234 between the distal surface 176 of the at least one column 172 and the proximal surface 232 of the flange 132 that is greater than zero. Next, the dose divider 106 and plunger 104 assembly may be translated toward the barrel 102 until the shortened column 172 bears on the barrel 102 in the second configuration, as shown in FIG. 6.

Alternatively, a remaining length 238 of at least one column 172 may be shortened by breaking away a sacrificial portion 334 of the at least one column 172 at a corresponding frangible link 330 (see FIG. 3D) while the dose divider 106 is installed on the plunger 104, thereby returning the syringe assembly to its first configuration as shown in FIG. 5, without removing the dose divider 106 from the plunger 104. As a result, the dose divider 106 may exhibit a renewed distance 234 between the distal surface 176 of the at least one column 172 and the proximal surface 232 of the flange 132 that is greater than zero. Next, the dose divider 106 and plunger 104 assembly may be translated toward the barrel 102 until the shortened column 172 bears on the barrel 102 in the second configuration, as shown in FIG. 6.

Moreover, the remaining length 238 of one or more columns 172 of the dose divider 106 may be successively shortened in any number of shortening steps by breaking away further sacrificial portions of one or more columns 172 of the dose divider 106 during operation of the syringe 100. Accordingly, successive shortening of the remaining length 238 of one or more columns 172 may facilitate metering successive doses of fluid discharged from the syringe 100.

Figure 7:
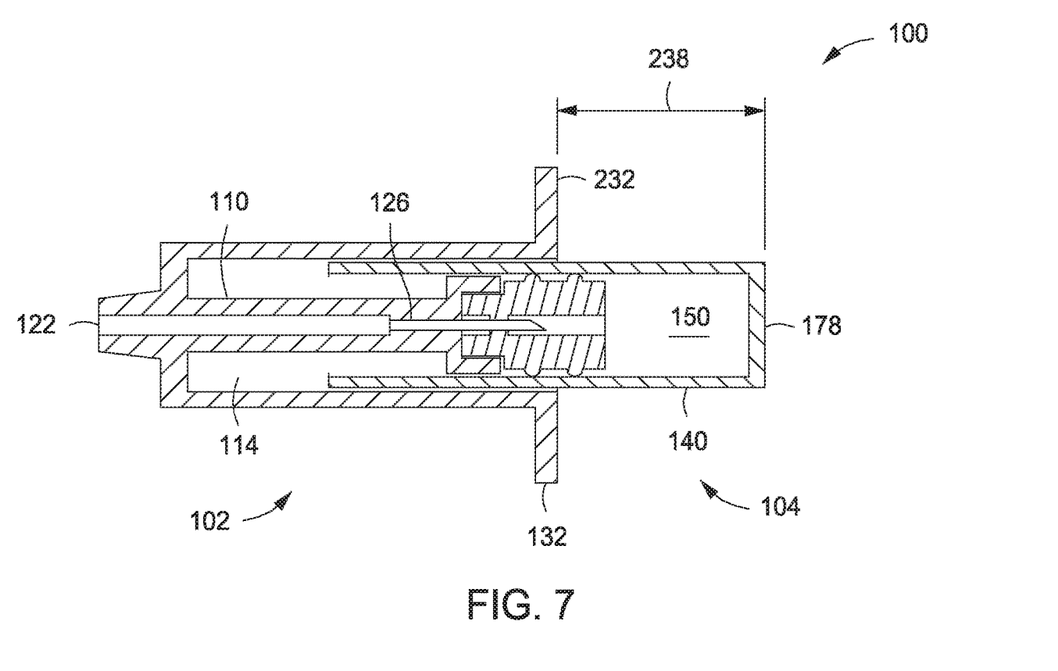
FIG. 7 shows a front cross sectional view of a syringe arranged in a third configuration, according to an aspect of the disclosure.

FIG. 7 shows a front cross sectional view of a syringe 100 arranged in a third configuration, according to an aspect of the disclosure. The vial 140 is in the same, or substantially the same, location relative to the barrel 102 as the second configuration illustrated in FIG. 6; however, in FIG. 7 the dose divider 106 has been removed from the plunger 104. The dose divider 106 may have been removed from the plunger 104 by translating the dose divider 106 relative to the plunger 104 along the longitudinal direction 130, the radial direction 134, or combinations thereof. According to an aspect of the disclosure, the proximal end 178 of the vial 140 is spaced apart from the proximal surface 232 of the flange 132 by the distance 238, when the syringe is in its third configuration.

Figure 8:
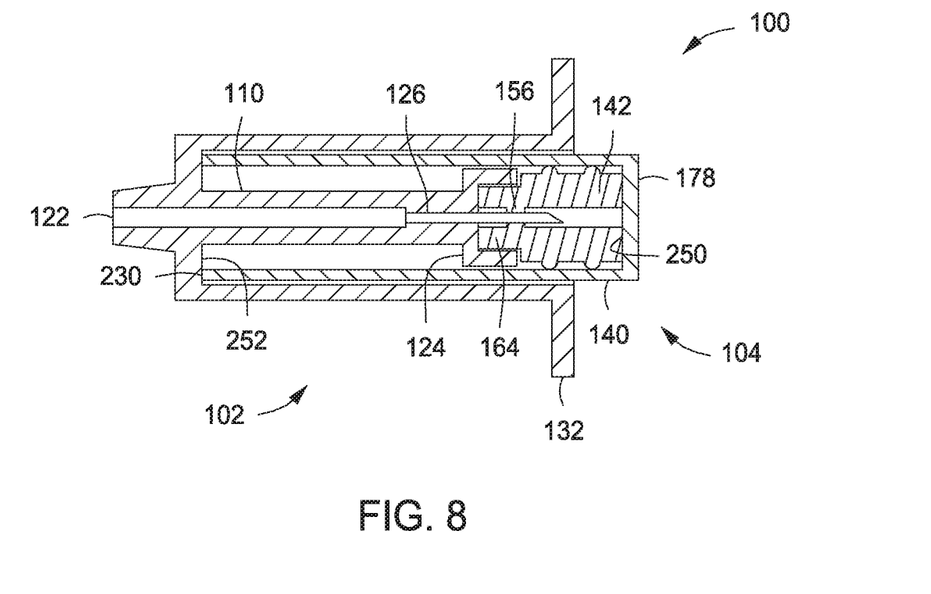
FIG. 8 shows a front cross sectional view of a syringe arranged in a fourth configuration, according to an aspect of the disclosure.

FIG. 8 shows a front cross sectional view of a syringe 100 arranged in a fourth configuration, according to an aspect of the disclosure. Similar to the third configuration of the syringe 100 in FIG. 7, the fourth configuration of the syringe 100 in FIG. 6 has the piston connector 164 coupled with the stem connector 124, such that the cannula 126 pierces through the septum 156 of the piston 142. However, in the fourth configuration illustrated in FIG. 8, the vial 140 has been further translated toward the distal aperture 122 of the inner stem 110 along the longitudinal direction 130, such that a proximal surface 250 of the internal surface 144 of the vial 140 bears on the piston 142, the distal end 230 of the vial 140 bears on a distal surface 252 of the internal surface 112 of the barrel 102, or combinations thereof. Thus, between the third configuration (see FIG. 7) and the fourth configuration of the syringe 100, a subsequent portion of the material contained within the fluid chamber 150 (see FIG. 7) is delivered out of the syringe 100 via the distal aperture 122 of the inner stem 110. According to an aspect of the disclosure, a quantity of the subsequent portion of material delivered by the syringe 100 is substantially equal to a quantity of the first portion of material delivered by the syringe 100.

The present disclosure is applicable to syringes in general, and more particularly, to syringes that provide tactile feedback to the user of material quantity delivered from the syringes. Further, the present disclosure may be applicable to syringes used in the context of medicine, manufacturing, construction, maintenance and repair, agriculture, food preparation, or any other context where syringes may be used. Accordingly, aspects of the disclosure may be applied to syringes for delivering a medication to a patient, or delivering other fluid materials such as air, adhesives, lubricants, food products, and the like.

Although FIGS. 2 and 5-8 show a vial-type syringe, where the distal aperture 122 is in fluid communication with a vial via a cannula 126 that pierces a septum 156 of a piston 142, it will be appreciated that the present disclosure may benefit other syringe types or structures. For example, the dose divider 106 may be advantageously incorporated into a syringe structure where an external surface of the plunger 104 defines a sealing surface in sliding engagement with the internal surface 112 of the barrel, and where the syringe does not include the cannula 126 or the vial 140. Further, it will be appreciated that aspects of the present disclosure may beneficially apply to any syringe structure where translation of a plunger 104 relative to a syringe body 102 expels a fluid from the distal aperture 122 of the syringe body 102.

Applicants have identified a need for delivering multiple doses of medication from a single syringe using rapid plunger motion to deliver each of the multiple doses. For example, nasal administration of medications may benefit from delivery of partial doses to each nostril of a patient in quick succession and with a high degree of atomization.

The degree of atomization increases with increasing pressure drop across the atomization orifice, and therefore, increasing flow rate through the atomization orifice. Accordingly, the degree of atomization may benefit from higher velocities of the plunger 104 relative to the barrel 102 during medicine delivery. In turn, Applicants have discovered that high plunger velocities for multi-dose syringes may result in repeatability and reproducibility errors, in both the amount of medicine in each dose and the degree of atomization, when dose quantity is controlled via visual feedback of a relative position of the plunger 104 within the barrel 102 of the syringe 100. Indeed, errors in dose quantity based on visual feedback may be exacerbated by the need for high plunger velocities at least because of difficulty in rapidly decelerating the plunger 104 while simultaneously stopping precisely at the longitudinal location corresponding to a desired dose.

Aspects of the disclosure address drawbacks of conventional approaches by providing tactile dose feedback through variable interference between the dose divider 106 and the barrel 102 of a syringe 100, using an economical and intuitive structure. As described previously, the dose divider 106 is removably coupled to the plunger 104 to provide variable degrees of tactile interference between the dose divider 106 and the barrel 102. Indeed, by providing variable degrees of interference between the dose divider 106 and the barrel 102 to limit the individual dose quantities, syringe users may allocate more attention to the rate of plunger travel and the location of the distal aperture 122 of the syringe 100 relative to a patient's nose, thereby improving repeatability and reproducibility of both dose quantity and the degree of atomization.

In addition, Applicants discovered advantages to providing geometric flexibility in the dose divider 106 by providing frangible links 320, which may be used by operators to tailor the working lengths of columns 172 on the dose divider 106 by breaking sacrificial portions 334 of the columns 172 away from the columns 172, thereby shortening the respective column 172. Accordingly, a single dose divider 106 design may be used to meter a myriad of fluid dose quantities from a syringe 100.

Further aspects of the disclosure provide a syringe kit, including a barrel 102, a pre-filled vial 140, and a dose divider 106, where a user assembles the kit to construct a syringe 100 according to aspects of the disclosure.

The syringe 100 may be configured such that the first portion of material delivered from the syringe 100 may be substantially equal in quantity to a second or otherwise subsequent portion of material delivered from the syringe 100. However, it will be appreciated that the syringe 100 may also be configured such that the quantity of the first portion of material is different from the quantity of a subsequent portion of material for other material delivery processes.

Unless specified otherwise herein, the word "substantially" shall mean "considerable in extent," or shall mean "largely but not necessarily wholly that which is specified."

It will be appreciated that the foregoing description provides examples of the disclosed apparatus and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The invention claimed is:

1. A dose divider for a syringe, the dose divider comprising:

a base including a flange that extends at least partly in a radial direction; and at least one column extending away from the base along a longitudinal direction, the longitudinal direction being perpendicular to the radial direction, the at least one column including a proximal end and a distal end opposite the proximal end, the proximal end of the at least one column being coupled to the base, and the at least one column including a sacrificial portion coupled to a frangible link;

wherein the base further includes a wall extending away from the flange along the longitudinal direction, wherein the proximal end of the at least one column is coupled to the base via the wall, and wherein the wall is an annular wall, and an interior surface of the annular wall defines a recess therein.

2. The dose divider of claim 1, wherein the at least one column is coupled to the base via the frangible link.

3. The dose divider of claim 2, wherein the at least one column further includes a fixed portion coupled to the sacrificial portion via the frangible link, the fixed portion being coupled to the base.

4. A dose divider for a syringe, the dose divider comprising:

a base including a flange that extends at least partly in a radial direction; and at least one column extending away from the base along a longitudinal direction, the longitudinal direction being perpendicular to the radial direction, the at least one column including a proximal end and a distal end opposite the proximal end, the proximal end of the at least one column being coupled to the base, and the at least one column including a sacrificial portion coupled to a frangible link;

wherein the at least one column includes a first column and a second column, a length of the first column along the longitudinal direction being greater than a length of the second column along the longitudinal direction, and wherein the at least one column further includes a third column, the length of the second column along the longitudinal direction being greater than a length of the third column along the longitudinal direction.

5. The dose divider of claim 4, wherein the at least one column is coupled to the base via the frangible link.

6. The dose divider of claim 5, wherein the at least one column further includes a fixed portion coupled to the sacrificial portion via the frangible link, the fixed portion being coupled to the base.

7. A dose divider for a syringe, the dose divider comprising:
a base including a flange that extends at least partly in a radial direction; and
at least one column extending away from the base along a longitudinal direction, the longitudinal direction being perpendicular to the radial direction,
the at least one column including a proximal end and a distal end opposite the proximal end, the proximal end of the at least one column being coupled to the base, and
the at least one column including a sacrificial portion coupled to a frangible link;
wherein the at least one column includes a first pair of columns, and
wherein a first column and a second column compose the first pair of columns, a length of the first column along the longitudinal direction being equal to a length of the second column along the longitudinal direction.

8. The dose divider of claim 7, wherein the first column is diametrically opposed to the second column across the base.

9. The dose divider of claim 7, wherein the at least one column further includes a second pair of columns,
wherein a third column and a fourth column compose the second pair of columns, a length of the third column along the longitudinal direction being equal to a length of the fourth column along the longitudinal direction, and
wherein the length of the first column is less than the length of the third column.

10. The dose divider of claim 9, wherein the third column is diametrically opposed to the fourth column across the base, and the third column is arranged between the first column and the second column about a circumferential direction.

11. The dose divider of claim 9, wherein the at least one column further includes a third pair of columns,
wherein a fifth column and a sixth column compose the third pair of columns, a length of the fifth column along the longitudinal direction being equal to a length of the sixth column along the longitudinal direction, and
wherein the length of the third column is less than the length of the fifth column.

12. The dose divider of claim 11, wherein the fifth column is diametrically opposed to the sixth column across the base, and the fifth column is arranged between the first column and the third column about a circumferential direction.

13. The dose divider of claim 7, wherein the at least one column is coupled to the base via the frangible link.

14. The dose divider of claim 13, wherein the at least one column further includes a fixed portion coupled to the sacrificial portion via the frangible link, the fixed portion being coupled to the base.

15. A dose divider for a syringe, the dose divider comprising:
a base including a flange that extends at least partly in a radial direction; and
at least one column extending away from the base along a longitudinal direction, the longitudinal direction being perpendicular to the radial direction,
the at least one column including a proximal end and a distal end opposite the proximal end, the proximal end of the at least one column being coupled to the base, and
the at least one column including a sacrificial portion coupled to a frangible link;
wherein a cross-sectional area of the sacrificial portion perpendicular to the longitudinal direction is greater than a cross-sectional area of the frangible link perpendicular to the longitudinal direction.

16. The dose divider of claim 15, wherein the at least one column is coupled to the base via the frangible link.

17. The dose divider of claim 16, wherein the at least one column further includes a fixed portion coupled to the sacrificial portion via the frangible link, the fixed portion being coupled to the base.

18. A dose divider for a syringe, the dose divider comprising:
a base including a flange that extends at least partly in a radial direction; and
at least one column extending away from the base along a longitudinal direction, the longitudinal direction being perpendicular to the radial direction,
the at least one column including a proximal end and a distal end opposite the proximal end, the proximal end of the at least one column being coupled to the base, and
the at least one column including a sacrificial portion coupled to a frangible link;
wherein the at least one column defines a concavity facing toward a longitudinal axis of the dose divider along the radial direction.

19. The dose divider of claim 18, wherein the at least one column is coupled to the base via the frangible link.

20. The dose divider of claim 19, wherein the at least one column further includes a fixed portion coupled to the sacrificial portion via the frangible link, the fixed portion being coupled to the base.

21. A syringe, comprising:
a barrel having an internal surface defining an internal bore therein;
a plunger having a distal end disposed within the internal bore of the barrel, and a proximal end disposed outside the internal bore of the barrel, the proximal end of the plunger being opposite the distal end of the plunger along a longitudinal direction; and
a dose divider configured to bear on the barrel in response to translation of the plunger relative to the barrel along the longitudinal direction, the dose divider including
a base including a flange that extends at least partly in a radial direction, the radial direction being perpendicular to the longitudinal direction; and
at least one column extending away from the base along the longitudinal direction,
the at least one column including a proximal end and a distal end opposite the proximal end, the proximal end of the at least one column being coupled to the base, and
the at least one column including a sacrificial portion coupled to a frangible link;
wherein a distal end of the barrel defines an outlet port, and
the plunger includes a vial having an internal volume, the internal volume being configured to contain a fluid, the internal volume of the vial being in fluid communication with the outlet port of the barrel.

22. The syringe of claim 21, wherein
the base of the dose divider defines an axis along the longitudinal direction,
the at least one column has a radial dimension from the axis to a point on the distal end of the at least one column, and the radial dimension of the at least one column is greater than a radial dimension from the axis to the internal bore of the barrel.

23. The syringe of claim 21, wherein
the barrel further includes a barrel flange disposed near a proximal end of the barrel, the barrel flange extending away from the barrel at least partly in the radial direction, and
a radial dimension of the at least one column is less than or equal to a radial dimension from the axis to a point on a periphery of the barrel flange.

24. The syringe of claim 23, wherein a distal surface of the at least one column faces the barrel flange, such that translation of the dose divider toward the barrel flange over a prescribed distance results in the distal surface of the at least one column bearing on the barrel flange.

25. A method for delivering a material from a syringe, the method comprising:
breaking away a first sacrificial portion from a first column of a dose divider at a first frangible link;
installing the dose divider on a proximal end of a plunger, such that a radially inner surface of a remaining column of the dose divider faces the plunger;
expelling a first portion of the material from the syringe by bearing a distal surface of a dose divider flange against a proximal surface of the plunger to translate the plunger from a first position to a second position relative to a barrel along a longitudinal axis of the plunger;
bearing a distal end of the dose divider against the barrel;
expelling a second portion of the material from the syringe by translating the plunger from the second position to a third position relative to the barrel along the longitudinal axis; and
rotating the dose divider relative to the barrel about a circumferential direction with respect to a longitudinal axis of the plunger, wherein the rotating the dose divider relative to the barrel occurs before the expelling the second portion of the material from the syringe.

26. The method of claim 25, wherein the remaining column is the first column after the breaking away of the first sacrificial portion.

27. The method of claim 25, wherein the breaking away the first sacrificial portion includes breaking away an entirety of a first column from the dose divider, and the remaining column is a second column of the dose divider, the second column being distinct from the first column.

28. The method of claim 25, wherein the remaining column is a first remaining column, and the distal end of the dose divider is a distal end of the first remaining column,
the method further comprising bearing a distal end of a second remaining column of the dose divider against the barrel,
wherein a length of the second remaining column along a longitudinal direction is shorter than a length of the first remaining column along the longitudinal direction, the longitudinal direction being parallel to the longitudinal axis of the plunger.

29. The method of claim 25, further comprising delivering the first portion of the material and the second portion of the material into an internal volume of a hollow portion of the plunger before expelling the first portion of the material from the syringe.

30. The method of claim 29, wherein the expelling the first portion of the material from the syringe includes expelling the first portion of the material from the internal volume of the plunger.

31. The method of claim 29, wherein the plunger includes a removable vial, and the internal volume of the plunger includes an internal volume of the removable vial.

* * * * *